United States Patent
Hsieh et al.

(10) Patent No.: US 11,142,795 B2
(45) Date of Patent: Oct. 12, 2021

(54) METHODS OF TREATING VIRAL INFECTION

(71) Applicant: Academia Sinica, Taipei (TW)

(72) Inventors: Shie-Liang Hsieh, Taipei (TW); Ya-Lang Huang, Taipei (TW); Tsung-Yu Tsai, Taipei (TW)

(73) Assignee: ACADEMIA SINICA, Taipei (TW)

( * ) Notice: Subject to any disclaimer, the term of this patent is extended or adjusted under 35 U.S.C. 154(b) by 79 days.

(21) Appl. No.: 16/491,163

(22) PCT Filed: Mar. 15, 2018

(86) PCT No.: PCT/US2018/022530
§ 371 (c)(1),
(2) Date: Sep. 5, 2019

(87) PCT Pub. No.: WO2018/170190
PCT Pub. Date: Sep. 20, 2018

(65) Prior Publication Data
US 2020/0010898 A1      Jan. 9, 2020

Related U.S. Application Data

(60) Provisional application No. 62/472,107, filed on Mar. 16, 2017.

(51) Int. Cl.
| | | |
|---|---|---|
| *G01N 33/53* | (2006.01) | |
| *A61K 38/21* | (2006.01) | |
| *C12Q 1/6883* | (2018.01) | |
| *C12Q 1/70* | (2006.01) | |
| *G01N 33/566* | (2006.01) | |
| *G01N 33/576* | (2006.01) | |

(52) U.S. Cl.
CPC ............ *C12Q 1/6883* (2013.01); *C12Q 1/706* (2013.01); *G01N 33/566* (2013.01); *G01N 33/5761* (2013.01); *C12Q 2600/158* (2013.01)

(58) Field of Classification Search
None
See application file for complete search history.

(56) References Cited

PUBLICATIONS

Hsieh et al. Academia Sinica Copyright 2005. "Plasma CLEC18 asthe biomarker for liver cirrhosis" 5 pages. (Year: 2005).*
Tsai et al. (2018). J. Biomed. Sci. 25:59 (10 pages).*

* cited by examiner

*Primary Examiner* — Joanne Hama
*Assistant Examiner* — Jon M Lockard

(57) ABSTRACT

Disclosed herein is a novel use of C-type lectin 18 (CLEC18) in disease prognosis. According to embodiments of the present disclosure, the mRNA or protein level of CLEC18 may serve as an indicator for diagnosing hepatitis B virus (HBV) infection, hepatitis B e antigen (HBeAg) loss and seroconversion, and/or liver fibrosis.

3 Claims, 5 Drawing Sheets
Specification includes a Sequence Listing.

METHODS OF TREATING VIRAL INFECTION

CROSS-REFERENCE TO RELATED APPLICATIONS

This application is a U.S. National Stage Filing under 35 U.S.C. 371 from International Patent Application Serial No. PCT/US18/22530, filed Mar. 15, 2018, and published on Sep. 20, 2018, which claims the priority of U.S. Ser. No. 62/472,107, filed Mar. 16, 2017, the disclosure of which are incorporated by reference herein in their entireties.

BACKGROUND OF THE INVENTION

1. Field of the Invention

The present disclosure in general relates to the field of disease diagnosis. More particularly, the present disclosure relates to methods of diagnosing hepatitis B virus (HBV) infection and/or the disorder associated with or caused by HBV infection.

2. Description of Related Art

HBV infection is a global health problem, affecting more than 2 billion people worldwide. It can cause both acute and chronic infections. Adults infected with HBV usually develop an acute infection. Most people do not experience any symptoms during the acute infection phase; however, some people have acute illness with symptoms, for example, loss of appetite, fatigue, nausea, vomiting, abdominal pain, fever and jaundice. The illness usually lasts for a few weeks and then gradually improves in most affected people. The prevalence of chronic HBV infection is about 5% worldwide that may slightly vary with factors, such as age, immune status, region and HBV genotype. The chronic infection is responsible for most HBV-related morbidity and mortality. The diseases or disorders associated with and/or caused by HBV infection include chronic hepatitis, cirrhosis, liver failure, and hepatocellular carcinoma (HCC).

In structure, HBV comprises an outer protein coating (hepatitis B surface antigen, HBsAg) and a nucleocapsid comprising the hepatitis B core antigen (HBcAg). Another protein, termed hepatitis B e antigen (HBeAg), is found in soluble form in sera of patients when virus is actively produced, either during acute or chronic infection. As an indicator or viral replication, HBeAg loss and seroconversion (i.e., the development of anti-HBe antibody) are defined as an intermediate therapeutic endpoint in HBeAg-positive patients. Evaluating the treatment outcome, status of liver fibrosis is important for chronic hepatitis B (CHB) patients. Clinically, a decline in HBV DNA levels during treatment and high serum alanine aminotransferase (ALT) level can predict HBeAg loss and HBeAg seroconversion. To assess the stage of liver fibrosis, liver biopsy is the gold standard method with the disadvantage of a high complication rate; noninvasive methods used biomarkers such as HBsAg, serum ALT levels, and scoring systems as FIB-4 and APRI. Those mentioned above have limitations as independent disease markers. In addition, other immune markers such as TNF-alpha, PD-1 and serum markers, such as apolipoprotein and haptoglobulin, are not specific for HBV disease and can easily be influenced by other diseases. Biomarkers for treatment outcome of HBV infection and liver fibrosis are still under development.

In view of the foregoing, there exists in the related art a need for a novel biomarker useful in diagnosing HBV infection and/or the disorder (e.g., liver fibrosis) associated with or caused by HBV infection.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a method of determining whether a subject is infected by HBV via a biological sample isolated from the subject. The method comprises,
 (a) measuring the messenger RNA (mRNA) or protein level of C-type lectin 18 (CLEC18) in the biological sample; and
 (b) determining whether the subject is infected by HBV based on the mRNA or protein level of CLEC18 measured in step (a), wherein when the mRNA or protein level of CLEC18 is lower than that of a healthy subject, then the subject is infected by HBV.

According to embodiments of the present disclosure, the biological sample may be a whole blood sample, a serum sample, a plasma sample, a central spinal fluid sample, a urine sample, a saliva sample or a biopsy sample.

According to some embodiments of the present disclosure, the biological sample is a biopsy sample. According to certain embodiments of the present disclosure, the biological sample is a plasma sample, in which the protein level of CLEC18 in the healthy subject is about 1,000-5,000 pg/mL; preferably, about 2,300-3,900 pg/mL.

A second aspect of the present disclosure is directed to a method of determining the severity of liver fibrosis in a subject having chronic hepatitis B via a biological sample isolated from the subject. The method comprises,
 (a) measuring the protein level of CLEC18 in the biological sample; and
 (b) determining the severity of liver fibrosis in the subject based on the measured protein level of CLEC18 in step (a).

In certain embodiments of the present disclosure, the biological sample is a plasma sample, in which when the protein level of CLEC18 is lower than 320 pg/mL, then the subject has severe fibrosis; in the case when the protein level of CLEC18 is or above 320 pg/mL, then the subject has no, mild or moderate fibrosis.

The CLEC18 may be CLEC18A (Protein ID: NP_872425.2), CLEC18B (Protein ID: NP_001011880.2), or CLEC18C (Protein ID: NP_775890.2), in which CLEC18A is encoded by gene clec18a (Gene ID 348174; NM_182619.3), CLEC18B is encoded by gene clec18b (Gene ID 497190; NM_001011880.2), and CLEC18C is encoded by gene clec18c (Gene ID 283971; NM_173619). According to one working example of the present disclosure, the CLEC18 is CLEC18A.

The subject suitable to be assessed by the methods in accordance with any aspect and embodiment of the present disclosure is preferably a human.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

DETAILED DESCRIPTION OF THE INVENTION

Figure 1A:
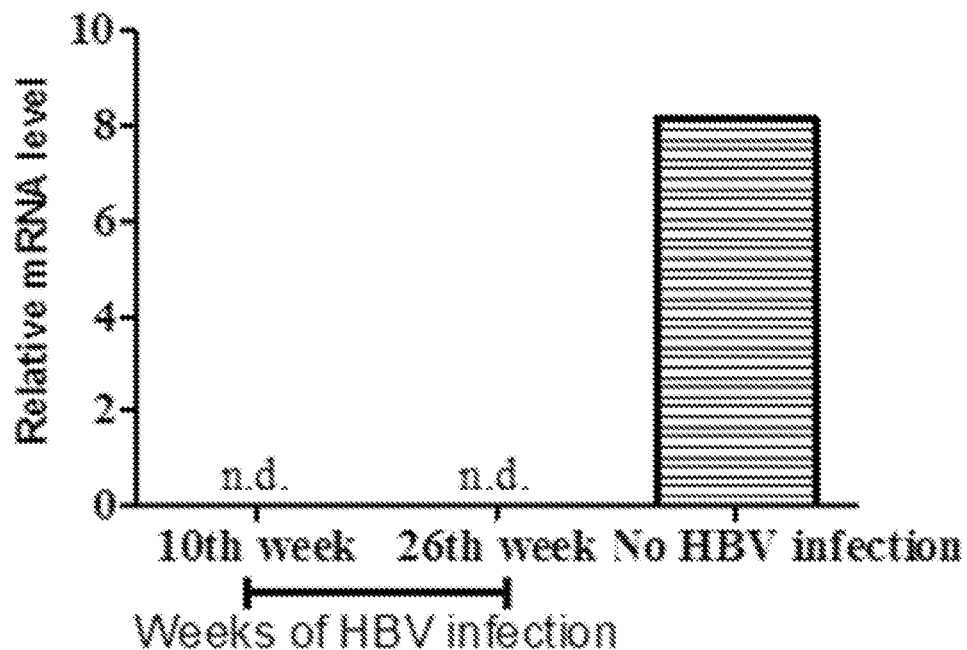
FIGS. 1A and 1B are histograms that respectively depict the expression level of human and mouse CLEC18 in human liver chimeric mice infected by HBV according to one embodiment of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "administered", "administering" or "administration" are used interchangeably herein to refer a mode of delivery, including, without limitation, orally, intravenously, intramuscularly, intraperitoneally, intraarterially, intracranially, or subcutaneously administering an agent (e.g., the nucleos(t)ide analogue or the anti-fibrotic agent).

As used herein, the term "treat," "treating" and "treatment" are interchangeable, and encompasses partially or completely preventing, ameliorating, mitigating and/or managing a symptom, a secondary disorder or a condition associated with HBV infection. The term "treating" as used herein refers to application or administration of one or more active agents to a subject, who has a symptom, a secondary disorder or a condition associated with HBV infection, with the purpose to partially or completely alleviate, ameliorate, relieve, delay onset of, inhibit progression of, reduce severity of, and/or reduce incidence of one or more symptoms, secondary disorders or features associated with HBV infection. Symptoms, secondary disorders, and/or conditions associated with HBV infection include, but are not limited to, loss of appetite, fatigue, nausea, vomiting, abdominal pain, fever and jaundice. Treatment may be administered to a subject who exhibits only early signs of such symptoms, disorder, and/or condition for the purpose of decreasing the risk of developing the symptoms, secondary disorders, and/or conditions associated with HBV infection.

The term "effective amount" as referred to herein designate the quantity of a component which is sufficient to yield a desired response. For therapeutic purposes, the effective amount is also one in which any toxic or detrimental effects of the component are outweighed by the therapeutically beneficial effects. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/Kg). Alternatively, the effective amount can be expressed in the concentration of the active component (e.g., the nucleos(t)ide analogue or the anti-fibrotic agent), such as molar concentration, mass concentration, volume concentration, molality, mole fraction, mass fraction and mixing ratio.

As used herein, the term "prognosis" refers to a prediction of treatment outcome, for example, a good or poor outcome (e.g., likelihood of long-term treatment). As could be appreciated, "prognosis" does not refer to the ability to predict the course or outcome of a condition with 100% accuracy. Instead, persons having ordinary skills in the art would understand that the term "prognosis" refers to an increased probability that a certain course or outcome will occur; that is, that a course or outcome is more likely to occur in a subject exhibiting a given condition (e.g., having the baseline protein level of CLEC18 between 320-2,000 pg/mL), when compared with those subjects not exhibiting the condition (e.g., having the baseline protein level of CLEC18 lower than 320 pg/mL or higher than 2,000 pg/mL). A favorable prognosis includes a prediction of good treatment outcome (e.g., HBeAg loss and/or seroconversion) or disease amelioration/stabilization (e.g., decreasing the expression level of HBeAg), while an unfavorable prognosis includes a prediction of poor treatment outcome or disease progression (e.g., drug-resistance or the development of liver fibrosis). Specifically, the term "favorable prognosis" refers to a prognosis determined for a subject having chronic hepatitis B which is better (i.e., has a more favorable outcome) than the prognosis for a reference subject or group of reference subjects with the same disease. For example, a subject having a favorable prognosis may be expected to have HBeAg loss and/or seroconversion in a shorter period of time (e.g., less than 2, 3, 4 or 5 years) relative to reference subjects. By contrast, the term "unfavorable prognosis" refers to a prognosis determined for a subject having chronic hepatitis B which is worse (e.g., has a less favorable outcome) than the prognosis for a reference subject or group of reference subjects with the same disease. For example, a subject having an unfavorable prognosis may be expected to have HBeAg loss and/or seroconversion in a longer period of time (e.g., more than 5 years) relative to reference subjects.

The term "baseline" refers to the information gathered at the beginning of a study from which the expression level evaluated in the study are measured. Specifically, the term "baseline" as used herein refers to the level of a protein (e.g., CLEC18) in a biological sample isolated from a subject before administration of the subject with a treatment; for example, IFN (including IFN-α and IFN-β), PEG-IFN (including PEG-IFNα and PEG-IFNβ), nucleos(t)ide analogue (including lamivudine, adefovir, entecavir, telbivudine, and tenofovir), or other treatments providing benefit in the treatment of HBV infection or the disorders associated with/caused by HBV infection.

The term "nucleoside analogue" refers to a compound which is similar to a nucleoside and is capable of inhibiting the metabolism of nucleic acid. The term "nucleotide analogue" refers to a non-natural occurring nucleotide, which may has, for example, altered sugar moieties, bases and inter-sugar linkages.

As used herein, the term "ex vivo" has its usual meaning in the art, and refers to an environment outside of a patient. More specifically, the term "ex vivo" refers to a reaction, a process or a method that are carried out in or on a biological sample isolated/obtained from a subject in an artificial environment outside the body of the subject from whom the biological sample has been obtained. The biological sample may be any sample taken from the subject from which the biomarker (i.e., CLEC18) of the current invention can be determined.

The term "patient" and "subject" are used interchangeably herein, and refer to a mammal including the human species that may be assessed by the methods of the present invention. The term "subject" is intended to refer to both the male and female gender unless one gender is specifically indicated.

The term "healthy subject" refers to a subject that does not have a disease (e.g., the subject has not been infected by HBV). For example, a healthy subject has not been diagnosed as having a disease and is not presenting with two or more (e.g., two, three, four or five) symptoms associated with the disease.

II. Description of the Invention

The present disclosure aims at providing novel methods for diagnosing HBV infection and/or the disorder (e.g., liver fibrosis) associated with or caused by HBV infection, and accordingly, rendering a subject in need thereof (for example, the subject having HBV or liver fibrosis) a suitable treatment regimen in time.

(i) Identification of HBV Infection

The first aspect of the present disclosure is thus directed to a method of determining whether a subject is infected by HBV. Specifically, the present invention provides a method for ex vivo diagnosis of HBV infection in a subject. The present method comprises obtaining a biological sample (e.g., a whole blood sample, a serum sample, a plasma sample, a central spinal fluid sample, a urine sample, a saliva sample or a biopsy sample, depending on desired purposes) from the subject; measuring the mRNA or protein level of CLEC18 in the biological sample; and determining whether the subject is infected by HBV based on the mRNA or protein level of CLEC18 measured.

According to embodiments of the present disclosure, when the mRNA or protein level of CLEC18 in the biological sample is lower than that of a healthy subject, then the subject is infected by HBV. In contrast, when the mRNA or protein level of CLEC18 in the biological sample is equal to or above that of a healthy subject, then the subject is infected by HBV.

The measured value may be expressed in either relative amount or absolute amount. The mRNA or protein level of CLEC18 in the biological sample may be measured by any assay commonly used or known by persons skilled in the art. For example, the protein level of CLEC18 can be measured by western blot analysis, enzyme-linked immunosorbent assay (ELISA), immunohistochemistry (IHC) assay, immunocytochemistry (ICC) assay, immunofluorescence (IF) assay, or luminex assay. According to one working example, the protein level of CLEC18 is determined by ELISA.

For the purposes of measuring the mRNA level, total RNA is first extracted from the biological sample by a chemical solution with high corrosiveness (e.g., phenol, trichloroacetic acid/acetone, and Trizol) followed by neutralization with chloroform. After centrifugation, the aqueous phase that contains the RNA sample is precipitated by an organic solution, such as ethanol and isopropanol. The RNA sample is then washed with ethanol to remove the contaminated protein followed by drying (e.g., air dry and vacuum dry) to obtain the RNA pellet. Then, the RNA pellet is dissolved in diethylpyrocarbonate-treated $H_2O$ (DEPC $H_2O$), and converted into the corresponding cDNA by reverse transcription (RT). In general, RT is performed by mixing the RNA with primer Oligo(dT)$_{20}$, deoxy-ribonucleoside triphosphate (dNTP, which comprises dATP, dGTP, dTTP, and dCTP), reverse transcriptase, reaction buffer, and optionally, the co-factor of reverse transcriptase (e.g., $MgCl_2$). Preferably, the reaction mixture further comprises dithiothreitol (DTT), a redox reagent used to stabilize the reverse transcriptase, and RNase inhibitor preventing the degradation of RNA during RT. The cDNA serving as a template may then be quantified by quantitative polymerase chain reaction assay (qPCR) or microarray (e.g., cDNA array and oligonucleotide array). According to one specific example, the mRNA level of CLEC18 is measured by qPCR.

In one working example, the biological sample is a liver biopsy sample, in which the mRNA level is measured by qPCR.

In some alternative examples, the biological sample is a plasma sample, in which the protein level of CLEC18 in the healthy subject is about 1,000-5,000 pg/mL. In other words, when the protein level of CLEC18 in the biological sample is lower than 1,000 pg/mL (<1,000 pg/mL), then the subject is infected by HBV. According to the preferred example, the protein level of CLEC18 in the healthy subject is about 2,300-3,900 pg/mL; that is, when protein level of CLEC18 in the biological sample is lower than 2,300 pg/mL (<2,300 pg/mL), then the subject is infected by HBV.

Based on the quantification result, a physician or a clinical practitioner may administer to a subject in need thereof (i.e., the subject having HBV infection) a suitable therapeutic regimen in time so as to treat the HBV infection and/or prevent the development/occurrence of disorders associated with/caused by HBV infection (e.g., liver fibrosis) in the subject.

(ii) Determination of Intermediate Therapeutic Endpoint

The second aspect of the present disclosure is directed to a method of making a prognosis of a treatment response in a subject. In particular, the present invention relates to a method for ex vivo making a prognosis of the response in a subject having chronic hepatitis B to a treatment. According to some embodiments of the present disclosure, the subject is an HBeAg-positive patient. According to certain embodiments of the present disclosure, the subject is an HBeAg-positive patient, who has not received any treatment. The method comprises obtaining a biological sample (e.g., a whole blood sample, a serum sample, a plasma sample, a central spinal fluid sample, a urine sample, a saliva sample or a biopsy sample, depending on desired purposes) from the subject; measuring the protein level of CLEC18 in the biological sample; and making a prognosis of the treatment response in the subject based on the measured protein level of CLEC18.

According to embodiments of the present disclosure, the protein level of CLEC18 is associated with HBeAg loss and HBeAg seroconversion. As mentioned above, HBeAg loss and HBeAg seroconversion are clinically defined as the intermediate therapeutic endpoints in patient having CHB. Thus, the physician or the clinical practitioner may decide whether or not to continuously administering the treatment to the subject in accordance with the protein level of CLEC18 thus measured.

According to some embodiments, the biological sample is a plasma sample. In these embodiments, the protein level of CLEC18 baseline between 320-2,000 pg/mL (i.e., 320 pg/mL≤the protein level of baseline CLEC18≤2,000 pg/mL) indicates a favorable prognosis for the subject. By contrast, the protein level of baseline CLEC18 lower than 320 pg/mL (<320 pg/mL) or higher than 2,000 pg/mL (>2,000 pg/mL) indicates an unfavorable prognosis for the subject. According to the embodiments, compared with the subject having the protein level of CLEC18 lower than 320 pg/mL or higher than 2,000 pg/mL, the subject having the protein level of CLEC18 between 320-2,000 pg/mL exhibits HBeAg loss and/or HBeAg seroconversion in a shorter period of time, for example less than 2 years.

The treatment may be IFN (including IFN-α and IFN-β), PEG-IFN (including PEG-IFNα and PEG-IFNβ), nucleos(t)ide analogue, or other treatments providing benefit in the treatment of HBV infection or the disorders associated with/caused by HBV infection. Non-limiting nucleos(t)ide analogue include, lamivudine, adefovir, entecavir, telbivudine, and tenofovir. According to one embodiment, the treatment is to administering to the subject an effective amount of any of lamivudine, adefovir, entecavir, telbivudine, or tenofovir.

(iii) Determination of Severity of Liver Fibrosis

HBV infection is one of the leading causes of liver fibrosis resulted from excessive accumulation of extracellular matrix proteins (e.g., collagen). Advanced liver fibrosis results in cirrhosis, liver failure, and HCC. In clinical practice, the development of liver fibrosis is a major determinant on the severity of chronic hepatitis B, accordingly, monitoring its development in such patient is important for managing the disease on.

The third aspect of the present disclosure thus pertains to a method of determining the severity of liver fibrosis in a subject. More specifically, the present invention provides a method for ex vivo determining the severity of liver fibrosis in a subject having chronic hepatitis B. According to certain embodiments of the present disclosure, the subject is an HBeAg-positive or HBeAg-negative patient. The method comprises obtaining a biological sample (e.g., a whole blood sample, a serum sample, a plasma sample, a central spinal fluid sample, a urine sample, a saliva sample or a biopsy sample, depending on desired purposes) from the subject; measuring the protein level of CLEC18 in the biological sample; and determining the severity of liver fibrosis in the subject based on the measured protein level of CLEC18.

According to certain embodiments of the present disclosure, the biological sample is a plasma sample, in which in the case when the protein level of CLEC18 is lower than 320 pg/mL (<320 pg/mL), then the subject has significant fibrosis (METAVIR fibrosis stage F3) or cirrhosis (METAVIR fibrosis stage F4). In contrast, when the protein level of CLEC18 is or above 320 pg/mL (≥320 pg/mL), then the subject has no, mild or moderate fibrosis (METAVIR fibrosis stage F0, F1 or F2). Based on the analysis, a subject in need thereof (e.g., the subject has severe fibrosis or cirrhosis) may receive a suitable treatment in time.

(iv) Diagnostic Kit and Uses Thereof

Another aspect of the present disclosure pertains to a diagnostic kit for determining the protein level of CLEC18, in which the diagnostic kit comprises two antibodies, both of which exhibit binding affinity and specificity to CLEC18 (e.g., CLEC18A, CLEC18B and/or CLEC18C). The antibodies of the diagnostic kit may respectively serve as the capture and detection antibodies employed in an Enzyme-Linked ImmunoSorbent Assay (ELISA) thereby determining the protein level of CLEC18 in a biological sample. As mentioned above, the mRNA or protein level of CLEC18 is associated with HBV infection, HBeAg loss/seroconversion, and liver fibrosis. Accordingly, the present diagnostic kit is useful for ex vivo determining whether a subject is infected by HBV. According to embodiments of the present disclosure, the diagnostic kit is used to measure the protein level of CLEC18 in a biological sample (e.g., a plasma sample or a biopsy sample) isolated from the subject, in which when the protein level of CLEC18 of the subject is lower than that of a healthy subject, then the subject is infected by HBV.

The present diagnostic kit may also be used to ex vivo make a prognosis of a treatment response in a subject having chronic hepatitis B. Specifically, a biological sample (e.g., a plasma sample) is first isolated from the CHB subject, who has not received any treatment; the biological sample is then analyzed by the present diagnostic kit, in which the protein level of CLEC18 in the biological sample is quantified. According to embodiments of the present disclosure, when the protein level of CLEC18 is about 320-2,000 pg/mL, the subject has a good treatment response; alternatively, when the protein level is lower than 320 pg/mL or higher than 2,000 pg/mL, then the subject has a poor treatment response.

According to alternative example of the present disclosure, the present diagnostic kit is useful for ex vivo determining the severity of liver fibrosis in a subject having chronic hepatitis B. In this example, a biological sample (e.g., a plasma sample) isolated from the subject is analyzed by the present diagnostic kit so as to determine the protein level of the CLEC18 in the biological sample. When the protein level of CLEC18 is lower than 320 pg/mL, it indicates that the subject has severe fibrosis; when the protein level of CLEC18 is or above 320 pg/mL, it indicates that the subject has no, mild or moderate liver fibrosis.

In general, the subject suitable to be assessed by the method in accordance with any aspect and embodiment of the present disclosure is a mammal; preferably, a human.

The CLEC18 is any of CLEC18A (Protein ID: NP_872425.2), CLEC18B (Protein ID: NP_001011880.2), or CLEC18C (Protein ID: NP_775890.2), in which CLEC18A, CLEC18B and CLEC18C are respectively encoded by genes clec18a (Gene ID 348174; NM_182619.3), clec18b (Gene ID 497190; NM_001011880.2), and clec18c (Gene ID 283971; NM_173619). It is known that the amino acid sequences of CLEC18A, CLEC18B, and CLEC18C are almost identical, in which merely several amino acid residues located in the C-type lectin-like domain (CTLD) and the sperm-coating protein/Tpx-1/Ag5/PR-1/Sc7 (SCP/TAPS) domain are distinct from each other. In general, CLEC18A, CLEC18B and CLEC18C exhibit similar expression patterns in the subject. According to one working example of the present disclosure, the CLEC18 measured by the method and diagnostic kit as mentioned in any aspect and embodiment of the present disclosure is CLEC18A.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods

Infection of Human Liver Chimeric Mice with HBV

Human liver chimeric mice were generated by Fah$^{-/-}$/Rag2$^{-/-}$/Il2rg$^{-/-}$ mice (FRG mice) with transplanted human hepatocytes. Each human liver chimeric mouse was infected with HBV, produced by HBV transgenic mice using the hydrodynamic vein injection method. In brief, 6-week-old FRG mice were intrasplenically transplanted with human hepatocytes (BD Biosciences). HBV obtained from ICR/HBV transgenic mice was hydrodynamically injected into the FRG mice after 3-4 months transplantation. The mice were then sacrificed at 10 and 26 weeks after HBV infection, and liver samples were collected for analysis.

CLEC18 Detection of Human Liver Chimeric Mice with/without HBV Infection

Total RNA was extracted from liver tissues using Trizol according to the manufacturer's instructions (Invitrogen). The RNA was subjected to reverse transcription using a RevertAid™ First Strand cDNA Synthesis Kit (Fermentas), and was then used as the template for polymerase chain reaction (PCR) amplification. The CLEC18 cDNA levels in the liver tissue were quantified by real-time PCR, using hybridization probes (Roche Life Science; Table 1) with a thermocycler (LightCycler480®II, Roche).

TABLE 1

Hybridization probes for quantifying the expression of CLEC18

| Hybridization probes | Sequence | SEQ ID NO |
|---|---|---|
| H1 | 5'-GATCAAGAGCCAGAAAGTGCA-3' | 1 |
| H2 | 5'-GACATCCTCGCCTTCTATCTGGGCC-3' | 2 |
| H3 | 5'-GCAAAACCCGArAACCGTTACATCTGCC-3' | 3 |

Patients

271 NUC-naïve patients having CHB (101 positive and 170 negative for HBeAg) with indications were enrolled in this study. The inclusion criteria were age ≥20 years and a history of HBsAg carriage for more than 6 months. The exclusion criteria were liver diseases caused by other etiologies, HCC at baseline, comorbid diseases or cancer. Among those 101 HBeAg-positive patients, 80 received entecavir, 17 received tenofovir, 3 received telbivudine, and 1 received lamivudine. Of these patients, 56 achieved HBeAg loss and 36 achieved HBeAg seroconversion.

Laboratory Examination

Baseline plasma CLEC18 levels were measured by ELISA kit (code: CSB-EL005521HU; CUSABIO Life Science). Platelets were measured by DxH 800 system (Beckman Coulter); prothrombin time (PT) was measured by CS-2100i (Siemens Healthineers Global); the serum levels of albumin, total bilirubin, creatinine, ALT were determined by DxC 800 system (Beckman Coulter); and the serum level of alpha-fetoprotein (AFP) was measured by DxI 800 system (Beckman Coulter). Serum HBV DNA was detected by COBAS AmpliPrep-COBAS TaqMan HBV test (lower limit of detection, 12 IU/mL; Roche Diagnostic Systems, Branchburg, N.J., USA). HBeAg, anti-HBe antibodies and HBsAg were quantified by commercially available enzyme immunoassays (Abbott Diagnostics, Abbott Park, Ill., USA). Liver fibrosis (F) was staged according to the METAVIR system. Cirrhosis and fatty liver was defined on ultrasonographic analysis.

Cutoff Values Definition

The patients were assigned into three subgroups according to the similar values close to cutoff values of baseline plasma CLEC18 levels (319.52 and 2015.08 pg/mL, Risk estimate: 0.297) and baseline plasma HBsAg levels (2889.3-12022.2 IU/mL, Risk estimate: 0.366), which were associated with the highest rates of HBeAg loss in the patients with CHB receiving NUC therapy by using construct and Classification and Regression Tree (CART). The cutoff value for age (40 years) was defined as the median of the 101 patients, and the cutoff value for ALT (5×ULN) was set to 40 IU/L. The cutoff values for total bilirubin, PT, platelet and AFP were based on normal values, and the cutoff values for APRI and FIB-4 were determined by the sensitivity, specificity, and positive and negative predictive values for the fibrosis index. The calculation is described more fully in, for example, Lin Z H et al. (Hepatology 2011; 53:726-736) and Sterling R K et al. (Hepatology 2006; 43:1317-1325).

Therapeutic Endpoint

HBeAg loss was defined as the absence of serum HBeAg during NUC treatment, and HBeAg seroconversion was defined as HBeAg loss with the presence of anti-HBe antibodies.

Statistical Analysis

Continuous variables were compared between two groups using the t-test and Wilcoxon rank sum test, and presented as the median (interquartile range). Categorical variables were analyzed by chi-squared test. Linear regression analyses were used to identify factors associated with CLEC18 expression. Logistic regression analyses were used to identify factors associated with HBeAg loss, seroconversion, and liver pathologic fibrosis stage. Kaplan-Meier analysis and the log-rank test were used to compare the cumulative incidence rates of HBeAg loss and seroconversion in CHB patient subgroups. SAS version 9.4 (SAS Institute, Inc., Cary, N.C., USA) and SPSS (IBM Corp. Released 2013, IBM SPSS Statistics for Windows, Version 22.0. Armonk, N.Y.) were used for statistical analyses. A two-sided P value of <0.05 was considered as statistically significant.

Example 1 CLEC18 Expression was Down-Regulated by HBV

In this example, whether HBV infection would affect (e.g., increase or decrease) the expression of CLEC18 was examined by the mouse model and human patients. The results were respectively depicted in FIGS. 1A-1B and Tables 2-4.

Figure 1B:
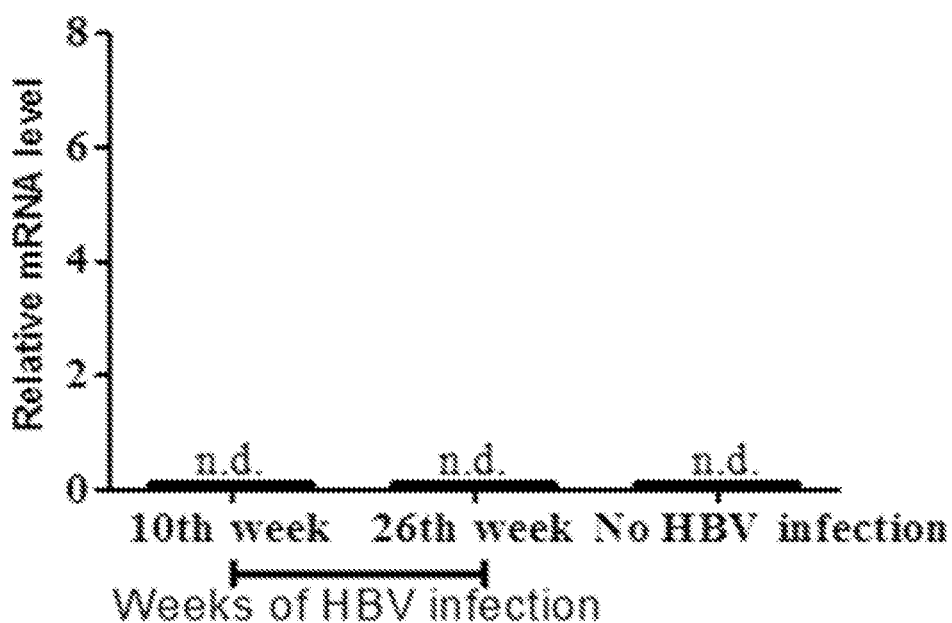

The relative mRNA expression levels of human CLEC18 were dramatically down-regulated in the liver tissues of HBV-infected human liver chimeric mice after 10 and 26 weeks infection compared to those non-infected controls (FIG. 1A). Mouse CLEC18 was not detected, indicating that the liver tissue collected contained only human liver (FIG. 1B). This finding suggested that the expression of CLEC18 in human hepatocytes was down-regulated by HBV.

To further examine the role of CLEC18 in different stages of CHB, the patients having CHB were assigned into four groups according to the presence of HBeAg and HBV DNA levels. The baseline patient characteristics are presented in Table 2. In brief, compared with the HBeAg-negative patients, the HBeAg-positive patients were significantly younger, had lower prevalence rates of genotype B infection and cirrhosis, and had higher platelet counts, ALT, HBV DNA, and HBsAg levels.

TABLE 2

Baseline patient characteristics

| Variables<br>Median ± IQR or N (%) | Total<br>(n = 271) | HBeAg-negative<br>(n = 170) | HBeAg-positive<br>(n = 101) | P Value |
|---|---|---|---|---|
| Age | 47 ± 14 | 51 ± 12 | 40 ± 13 | <0.0001 |
| Gender | | | | 0.6454 |
| Man | 187 (69.0) | 119 (70.0) | 68 (67.33) | |
| Woman | 84 (31.0) | 51 (30.0) | 33 (32.67) | |
| Genotype | | | | 0.0003 |
| B | 166 (62.88) | 118 (71.08) | 48 (48.98) | |
| C | 98 (37.12) | 48 (28.92) | 50 (51.02) | |
| HBsAg: log10 IU/mL | 3.29 ± 1.11 | 3.04 ± 0.76 | 3.86 ± 1.01 | <0.0001 |
| HBV DNA: log10 IU/mL | 7.72 ± 3.86 | 5.12 ± 4.05 | 8.58 ± 1.15 | <0.0001 |
| Cirrhosis | | | | 0.0028 |
| No | 182 (67.16) | 103 (60.59) | 79 (78.22) | |
| Yes | 89 (32.84) | 67 (39.41) | 22 (21.78) | |
| Fatty liver | | | | 0.2510 |
| No | 133 (49.08) | 88 (51.76) | 45 (44.55) | |
| Yes | 138 (50.92) | 82 (48.42) | 56 (55.45) | |
| Albumin: g/dL | 4.15 ± 0.62 | 4.1 ± 0.6 | 4.2 ± 0.6 | 0.2940 |
| ALT: IU/L | 97 ± 241 | 79.5 ± 183 | 154.0 ± 577 | 0.0007 |
| Total bilirubin: mg/dL | 1 ± 0.62 | 1 ± 0.64 | 1 ± 0.62 | 0.3043 |
| Platelet: × $10^3/\mu L$ | 161 ± 78 | 149.5 ± 64 | 183.0 ± 85 | <0.0001 |
| PT: seconds prolonged | 1.10 ± 2.0 | 0.91 ± 1.81 | 1.38 ± 2.12 | 0.1182 |
| Cr: mg/dL | 0.86 ± 0.29 | 0.86 ± 0.27 | 0.87 ± 0.28 | 0.4223 |
| AFP: ng/mL | 5.12 ± 7.19 | 4.65 ± 4.86 | 6.78 ± 12.19 | 0.2925 |
| Numbers of liver biopsy | 164 | 105 | 59 | |
| METAVIR Activity grade | | | | 0.5302 |
| 0.1 | 97 (59.15) | 64 (60.95) | 33 (55.93) | |
| 2.3 | 67 (40.85) | 41 (39.05) | 26 (44.07) | |
| METAVIR Fibrosis stage | | | | 0.0949 |
| 0-2 | 91 (57.59) | 52 (52.53) | 39 (66.10) | |
| 3.4 | 67 (42.41) | 47 (47.47) | 20 (33.90) | |

As summarized in Table 3, the mean plasma CLEC18 level in healthy donors (n=35) was 3,106 pg/mL; the mean CLEC18 level in treatment-naïve HBeAg-positive CHB patients with HBV DNA>2.0×10$^7$ IU/mL (n=101) was 663 pg/mL; the mean CLEC18 level in HBeAg-negative CHB patients with HBV DNA>2.0×10$^7$ IU/mL (n=65) was 281 pg/mL; the mean CLEC18 level in HBeAg-negative CHB patients with HBV DNA at 2,000-2.0×10$^7$ IU/mL (n=64) was 264 pg/mL; and the mean CLEC18 level in HBeAg-negative CHB patients with HBV DNA<2,000 IU/mL (n=41) was 113 pg/mL. The data indicated that the plasma CLEC18 level was significantly down-regulated in each HBV-infected group as compared to the healthy donors (P<0.001). Further, the plasma CLEC18 level in HBeAg negative group was significantly lower than that of HBeAg positive group (P<0.05). The plasma CLEC18 level did not vary with the viral load in HBeAg negative patients.

TABLE 3

Plasma CLEC18 levels in the patients with CHB

| Group (viral load IU/mL) | Number of patients | CLEC18 level (Mean ± SEM, pg/mL) | P value[1] | P value[2] |
|---|---|---|---|---|
| Healthy donors | 35 | 3106 ± 795.8 (about 2,300-3,900 pg/mL) | — | — |
| HBeAg-positive (>2 × 107) | 101 | 663.6 ± 136.9 (about 525-800 pg/mL) | <0.001 | — |
| HBeAg-negative (>2 × 107) | 65 | 281.7 ± 93.41 (about 185-375 pg/mL) | <0.001 | 0.0196 |
| HBeAg-negative (2000-2 × 107) | 64 | 264.7 ± 69.21 (about 195-335 pg/mL) | <0.001 | 0.0106 |
| HBeAg-negative (<2000) | 41 | 113.3 ± 36.18 (about 77-150 pg/mL) | <0.001 | 0.0057 |

P value[1]: Compared to healthy donors
P value[2]: Compared to HBeAg-positive (>2 × $10^7$) group The univariate and multivariate linear regression analyses were used to identify factors associated with plasma CLEC18 levels in the patients with CHB (Table 4). The univariate analysis revealed that age was negatively associated with plasma CLEC18 levels, and that HBeAg positivity, HBsAg, HBV DNA, and ALT levels were positively associated with plasma CLEC18 levels. The multivariate analysis identified age as a marginal independent factor associated with plasma CLEC18 levels.

The univariate analysis identified baseline ALT level>5× ULN, AFP>20 ng/mL, HBsAg level of 2,900-12,000 IU/mL, and plasma CLEC18 level of 320-2,000 pg/mL as the factors significantly associated with HBeAg loss (Table 5), and baseline ALT level>5×ULN and plasma CLEC18 level of 320-2,000 pg/mL as the factors significantly associated with HBeAg seroconversion (Table 6). The multivariate analysis identified baseline plasma CLEC18 level of 320-2,000 pg/mL as the independent predictors of HBeAg

TABLE 4

Factors associated with CLEC18 levels in the patients with CHB

| Variables | Univariate analysis | | | | Multivariate analysis | | | |
|---|---|---|---|---|---|---|---|---|
| | Parameter Estimate | Standard Error | T Value | P Value | Parameter Estimate | Standard Error | T Value | P Value |
| Age | −18.41386 | 5.17495 | −3.56 | 0.0004 | −11.3821 | 6.1275 | −1.86 | 0.0644 |
| Sex: Man vs Woman | −25.76591 | 128.98391 | −0.20 | 0.8418 | | | | |
| Genotype: C vs B | 29.89732 | 126.53368 | 0.24 | 0.8134 | | | | |
| HBeAg: (+) vs (−) | 428.94574 | 120.57574 | 3.56 | 0.0004 | 194.63847 | 162.600 | 1.20 | 0.2324 |
| HBsAg $\log_{10}$ IU/mL | 189.40927 | 67.77183 | 2.79 | 0.0056 | 20.737 | 91.28661 | 0.23 | 0.8205 |
| HBV DNA $\log_{10}$ IU/mL | 85.07892 | 27.25278 | 3.12 | 0.0020 | 25.6009 | 40.78698 | 0.63 | 0.5308 |
| Cirrhosis: Yes vs No | −142.57582 | 126.72962 | −1.13 | 0.2616 | | | | |
| Fatty liver: Yes vs No | −38.09601 | 119.31101 | −0.32 | 0.7497 | | | | |
| ALT: IU/L | 0.30495 | 0.14451 | 2.11 | 0.0358 | 0.09404 | 0.16072 | 0.59 | 0.5590 |
| Total bilirubin (mg/dL) | −5.61291 | 45.41720 | −0.12 | 0.9017 | | | | |
| Platelet: ×$10^3$/μL | 1.16809 | 0.97747 | 1.20 | 0.2331 | | | | |
| PT: seconds prolonged | −19.80886 | 31.83170 | −0.62 | 0.5343 | | | | |
| Cr: mg/dL | 17.03954 | 124.23906 | 0.14 | 0.8910 | | | | |
| AFP: ng/mL | 0.99144 | 0.79197 | 1.25 | 0.2117 | | | | |
| METAVIR Activity grade 2, 3 vs 0, 1 | −102.09187 | 167.92687 | −0.61 | 0.5441 | | | | |
| METAVIR Fibrosis stage 3, 4 vs 0-2 | −303.34073 | 171.59770 | −1.77 | 0.0791 | | | | |

Example 2 Prediction of HBeAg Loss and Seroconversion by CLEC18

The role of plasma CLEC18 in the prediction of HBeAg loss and seroconversion in the patients who have CHB and receive NUC treatment was examined in this example. The data were respectively depicted in FIGS. 2A-2D and summarized in Tables 5-8.

loss (odds ratio [OR]: 4.380, 95% confidence interval [CI]: 1.230-15.596, P=0.0226) and seroconversion (OR: 2.662, 95% CI: 1.002-7.071, P=0.0495) in the patients with CHB receiving NUC therapy. Baseline HBsAg level exhibiting significance in predicting HBeAg loss (Tables 5 and 6). The relative likelihood of achieving HBeAg loss or seroconversion among the subgroups of patients was further analyzed according to different baseline CLEC18 levels and HBsAg levels. Similarly, the baseline CLEC18 level of out of 320-2,000 pg/mL had a significantly lower OR of HBeAg loss and seroconversion, and the baseline HBsAg level of >12,000 IU/mL had a significantly lower OR of HBeAg loss (Tables 7 and 8).

TABLE 5

Factors associated with HBeAg loss in HBeAg-positive patients

| Variables | Univariate analysis | | Multivariate analysis | |
|---|---|---|---|---|
| | Odds Ratio (95% CI) | P Value | Odds Ratio (95% CI) | P Value |
| Age: ≥40 vs <40 years old | 0.800 (0.364-1.758) | 0.5786 | 1.200 (0.448-3.212) | 0.7170 |
| Sex: Woman vs Man | 1.660 (0.713-3.861) | 0.2397 | | |
| Genotype: C vs B | 1.049 (0.471-2.338) | 0.9070 | | |
| Cirrhosis: Yes vs No | 1.209 (0.464-3.153) | 0.6975 | | |
| HBsAg: 2,900-12000 vs <2,900 or >12000 IU/mL | 4.530 (1.648-12.451) | 0.0034 | 5.382 (1.722-16.820) | 0.0038 |
| HBV DNA: ≥8.3 vs <8.3 $\log_{10}$ IU/mL | 0.648 (0.287-1.465) | 0.2972 | | |
| ALT: ≥5× vs <5× ULN | 3.177 (1.391-7.254) | 0.0061 | 1.925 (0.684-5.417) | 0.2147 |
| Total bilirubin: ≥1.2 vs <1.2 mg/dL | 2.292 (0.998-5.260) | 0.0504 | 1.692 (0.568-5.039) | 0.3452 |
| PT: seconds prolonged | 1.176 (0.929-1.488) | 0.1780 | | |
| Platelet: ≥150 vs <150 × $10^3/\mu L$ | 0.997 (0.990-1.004) | 0.3375 | | |
| AFP: ≥20 vs <20 ng/mL | 4.000 (1.229-13.018) | 0.0213 | 3.666 (0.928-14.484) | 0.0639 |
| CLEC18: pg/mL | 1.000 (0.999-1.000) | 0.1640 | | |
| CLEC18: 320-2000 vs <320 or >2000 pg/mL | 4.800 (1.637-14.072) | 0.0043 | 4.380 (1.230-15.596) | 0.0226 |

TABLE 6

Factors associated with HBeAg seroconversion in the HBeAg-positive patients

| Variables | Univariate analysis | | Multivariate analysis | |
|---|---|---|---|---|
| | Odds Ratio (95% CI) | P Value | Odds Ratio (95% CI) | P Value |
| Age: ≥40 vs <40 years old | 0.721 (0.318-1.631) | 0.4321 | 1.118 (0.446-2.806) | 0.8117 |
| Sex: Woman vs Man | 0.889 (0.372-2.123) | 0.7908 | | |
| Genotype: C vs B | 1.676 (0.727-3.863) | 0.2253 | | |
| Cirrhosis: Yes vs No | 1.333 (0.506-3.513) | 0.5605 | | |
| HBsAg: 2,900-12000 vs <2,900 or >12000 IU/mL | 2.121 (0.876-5.136) | 0.0956 | 1.732 (0.670-4.476) | 0.2567 |
| HBV DNA: ≥8.3 vs <8.3 $\log_{10}$ IU/mL | 0.800 (0.340-1.880) | 0.6087 | | |
| ALT: ≥5× vs <5× ULN | 3.652 (1.546-8.626) | 0.0031 | 3.161 (1.255-7.960) | 0.0146 |
| Total bilirubin: ≥1.2 vs <1.2 mg/dL | 1.634 (0.713-3.742) | 0.2455 | | |
| PT: seconds prolonged | 1.002 (0.899-1.389) | 0.3158 | | |
| Platelet: ≥150 vs <150 × $10^3/\mu L$ | 1.016 (0.995-1.009) | 0.6128 | | |
| AFP: ≥20 vs <20 ng/mL | 1.000 (0.989-7.306) | 0.0525 | | |
| CLEC18: pg/mL | 1.000 (0.999-1.000) | 0.2455 | | |
| CLEC18: 320-2000 vs <320 or >2000 pg/mL | 3.506 (1.388-8.861) | 0.0080 | 2.662 (1.002-7.071) | 0.0495 |

TABLE 7

Factors associated with HBeAg loss stratified by different cutoff in HBeAg-positive patients

| Variable | Univariate analysis | | Multivariate analysis | |
|---|---|---|---|---|
| | Odds Ratio (95% CI) | P Value | Odds Ratio (95% CI) | P Value |
| Age: years old | | 0.5786 | | 0.9827 |
| <40 | 1.000 | | 1.000 | |
| ≥40 | 0.800 (0.364-1.758) | | 0.989 (0.349-2.803) | |
| ALT: IU/L | | 0.0061 | | 0.1514 |
| <200 | 1.000 | | 1.000 | |
| ≥200 | 3.177 (1.391-7.254) | | 2.229 (0.746-6.662) | |
| AFP: ng/mL | | 0.0213 | | 0.0752 |
| <20 | 1.000 | | 1.000 | |
| ≥20 | 4.000 (1.229-13.018) | | 3.548 (0.879-14.319) | |
| CLEC18: pg/mL | | | | |
| <320 | 0.231 (0.078-0.687) | 0.0084 | 0.250 (0.067-0.936) | 0.0395 |
| 320-2000 | 1.000 | | 1.000 | |
| >2000 | 0.102 (0.019-0.541) | 0.0073 | 0.112 (0.017-0.752) | 0.0243 |
| HBsAg: IU/mL | | | | |
| <2,900 | 0.277 (0.090-0.857) | 0.0438 | 0.277 (0.072-1.057) | 0.0603 |
| 2,900-12000 | 1.000 | | 1.000 | |
| >12000 | 0.181 (0.060-0.546) | 0.0142 | 0.148 (0.042-0.515) | 0.0027 |

TABLE 8

Factors associated with HBeAg seroconversion stratified by
different cutoff in the HBeAg-positive patients

| Variable | Univariate analysis | | Multivariate analysis | |
|---|---|---|---|---|
| | Odds Ratio (95% CI) | P Value | Odds Ratio (95% CI) | P Value |
| Age: years old | | 0.4321 | | 0.7731 |
| <40 | 1.000 | | 1.000 | |
| ≥40 | 0.721 (0.318-1.631) | | 0.868 (0.332-2.270) | |
| ALT: IU/L | | 0.0031 | | 0.0109 |
| <200 | 1.000 | | 1.000 | |
| ≥200 | 3.652 (1.546-8.626) | | 3.462 (1.331-9.005) | |
| CLEC18: pg/mL | | | | |
| <320 | 0.326 (0.127-0.834) | 0.0194 | 0.445 (0.161-1.232) | 0.1191 |
| 320-2000 | 1.000 | | 1.000 | |
| >2000 | 0.081 (0.009-0.741) | 0.0260 | 0.096 (0.010-0.946) | 0.0447 |
| HBsAg: IU/mL | | | | |
| <2,900 | 0.536 (0.192-1.496) | 0.6704 | 0.802 (0.254-2.527) | 0.7059 |
| 2,900-12000 | 1.000 | | 1.000 | |
| >12000 | 0.421 (0.154-1.154) | 0.2106 | 0.476 (0.159-1.427) | 0.1851 |

Figure 2A:
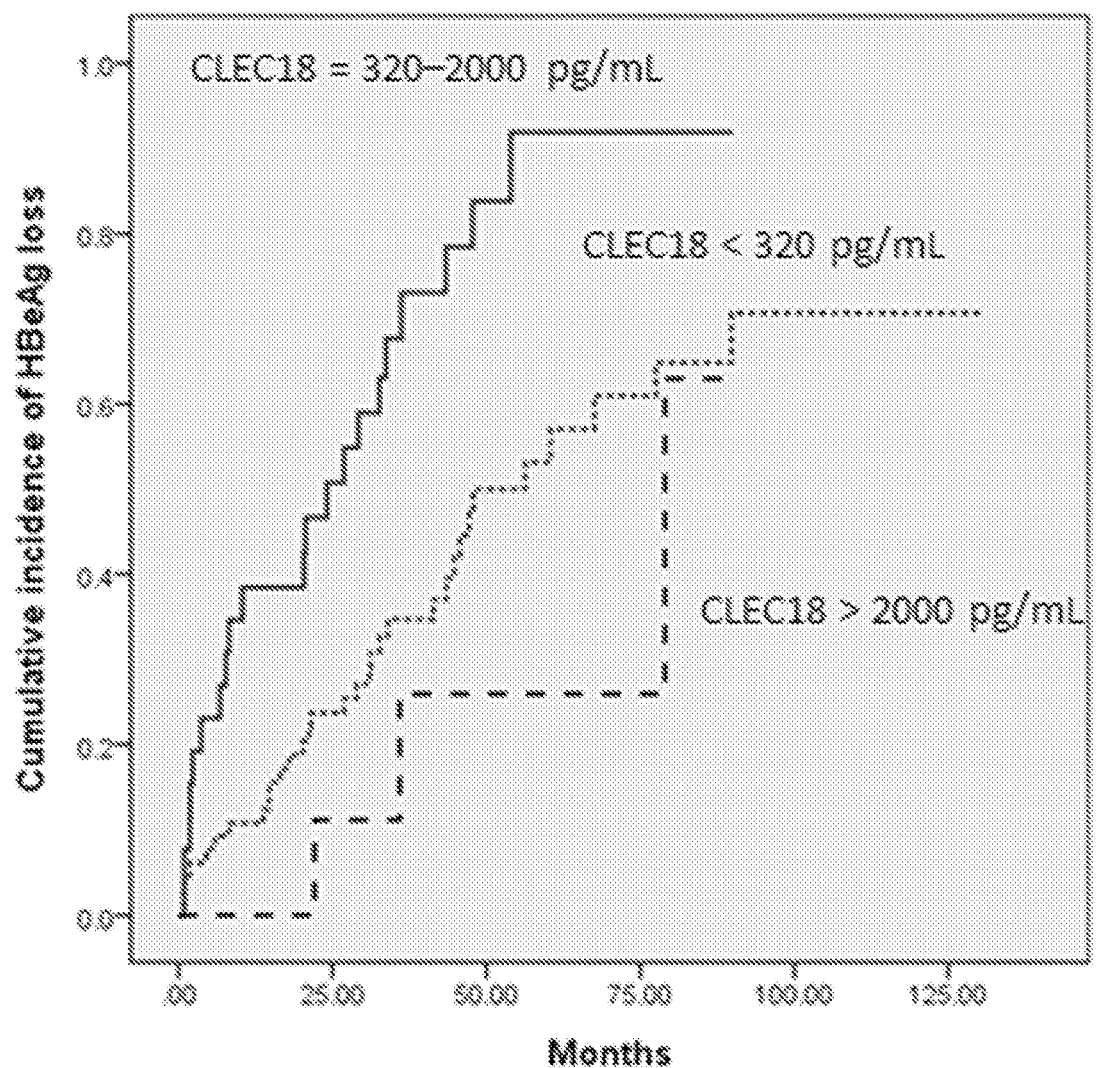
FIGS. 2A-2D are line charts that respectively depict the cumulative incidence rates of HBeAg loss and seroconversion according to another embodiment of the present disclosure. The HBeAg-positive patients receiving NUC therapy are assigned into specified groups based on the plasma level of CLEC18 (FIGS. 2A and 2B) or HBeAg (FIGS. 2C and 2D).
Figure 2B:
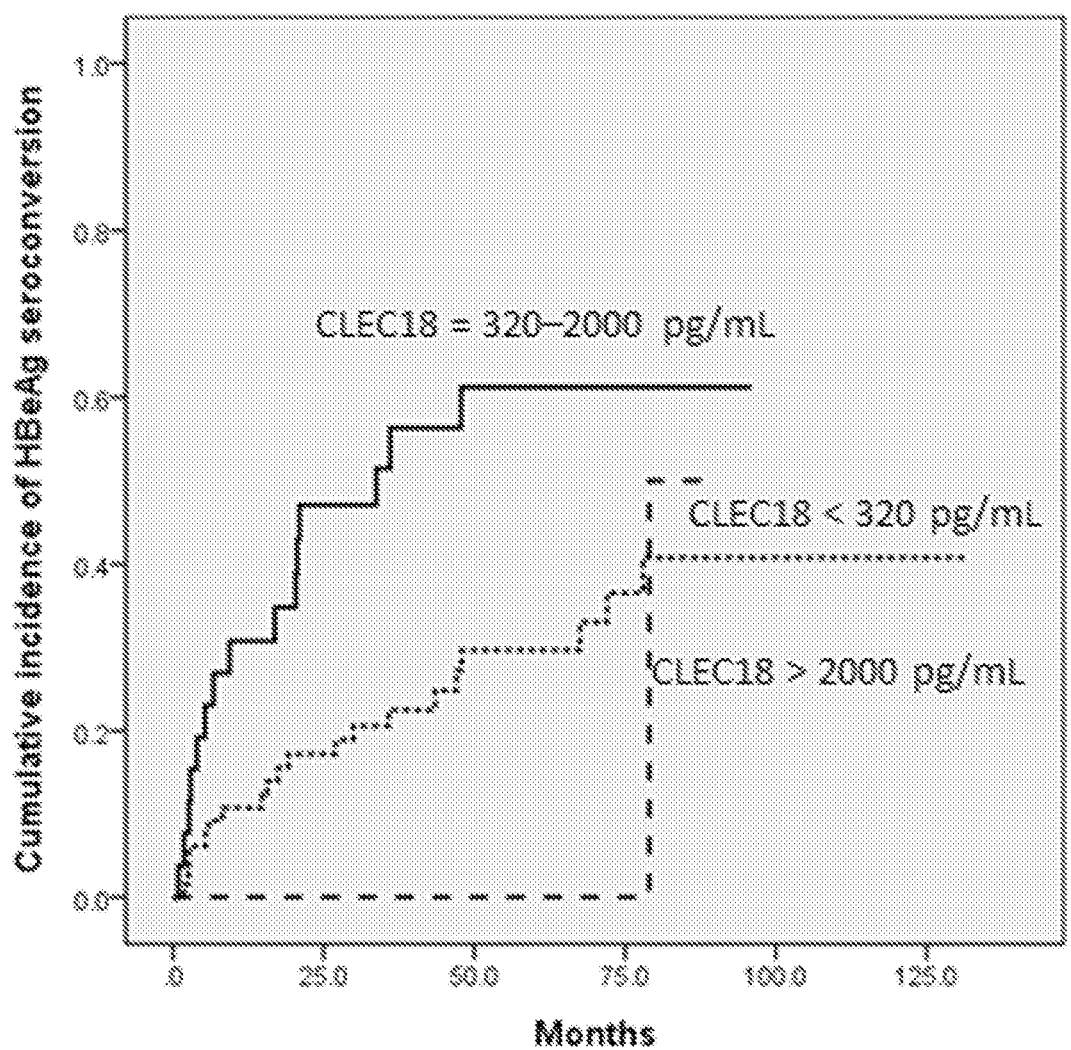
Figure 2C:
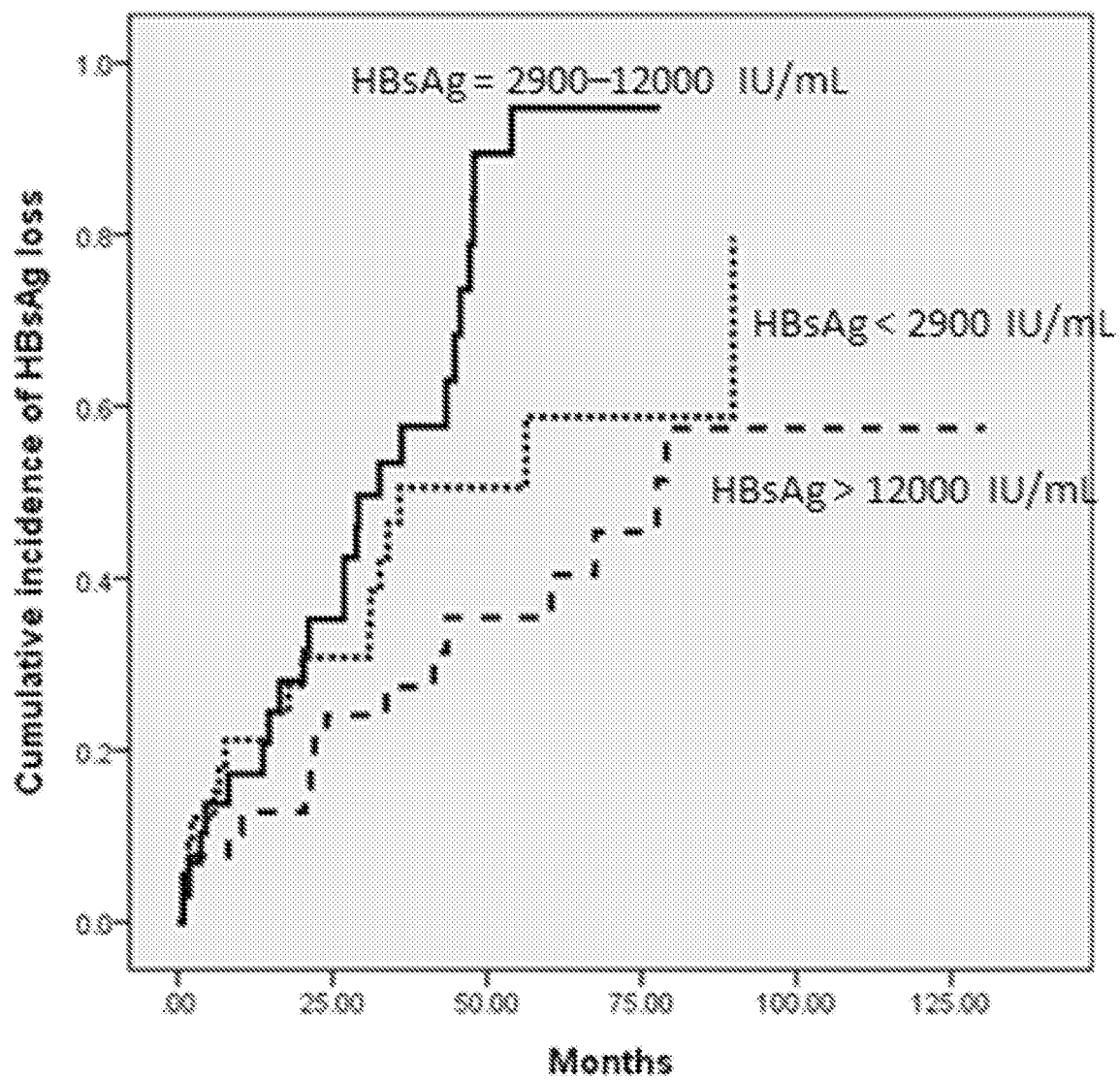
Figure 2D:
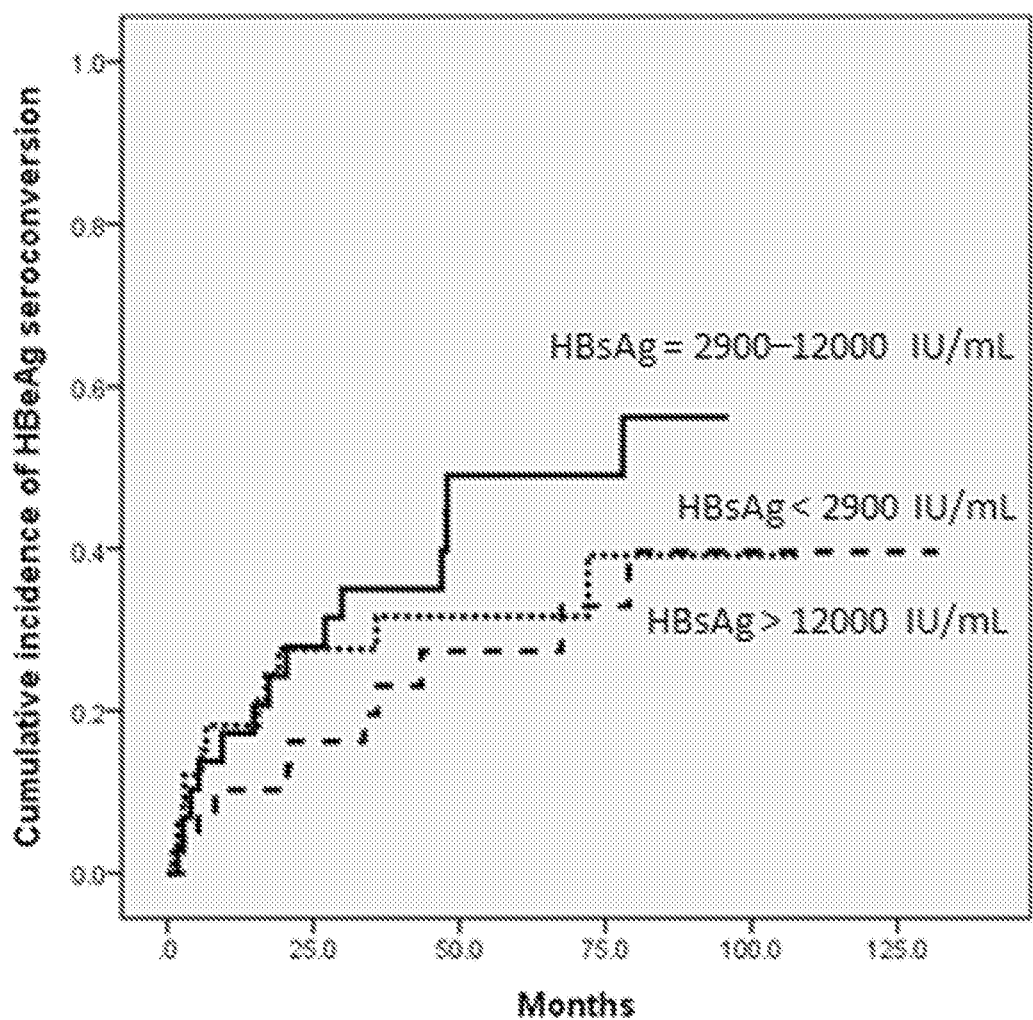

The cumulative incidence rates of HBeAg loss and seroconversion in the patients with CHB undergoing NUC therapy with a baseline plasma CLEC18 level of 320-2000 pg/mL were significantly higher than other patients (P<0.001 and P=0.002, respectively) (FIGS. 2A and 2B). The cumulative incidence of HBeAg loss but not HBeAg seroconversion in the patients with CHB undergoing NUC therapy with a baseline HBsAg level of 2,900-12000 IU/mL was significantly higher than other patients (P=0.027 and P=0.338 respectively) (FIGS. 2C and 2D).

Example 3 Correlation of Plasma CLEC18 and Baseline HBsAg Level

The relationship between CLEC18 and HBsAg level was analyzed in the HBeAg-positive patients. CLEC18 and HBsAg levels had a low Spearman's correlation coefficient (data not shown). However, patients with baseline plasma CLEC18 levels of <320, 320-2,000, and >2,000 pg/mL, the highest proportions had HBsAg levels of <2,900 (41.27%), 2,900-12,000 (44.44%) and >12,000 IU/mL (50%), respectively (Table 9, P=0.2558). The categorized plasma CLEC18 levels tended to be correlated with the categorized HBsAg levels in the HBeAg-positive patients with CHB.

TABLE 9

Correlation between HBsAg and CLEC18 levels

| CLEC18 level (pg/mL) | HBsAg level (IU/mL) | | | Total N = 100 (100%) |
|---|---|---|---|---|
| | <2900 | 2900-12000 | >12000 | |
| <320 | 26 (41.27%) | 17 (26.98%) | 20 (31.75%) | 63 (100%) |
| 320-2000 | 6 (22.22%) | 12 (44.44%) | 9 (33.33%) | 27 (100%) |
| >2000 | 2 (20.00%) | 3 (30.00%) | 5 (41.27%) | 10 (100%) |

Example 4 Correlation of Plasma CLEC18 Level and Liver Fibrosis

A total of 172 of the 271 enrolled CHB patients received a liver biopsy. The univariate analysis identified age>40 years, female sex, HBV genotype C, baseline HBsAg<3.0 $\log_{10}$ IU/mL, HBV DNA<6 $\log_{10}$ IU/mL, ALT<5×ULN, platelet<150×10³/uL, and baseline plasma CLEC18<320 pg/mL as the factors significantly associated with METAVIR fibrosis stages 3 and 4. In addition, baseline plasma CLEC18 level of <320 pg/mL tended to be better associated with METAVIR fibrosis stage compared to FIB-4 and APRI scores (Table 10).

TABLE 10

Factors associated with fibrosis stages 3 and 4 in the patients with CHB

| Variables | Univariate analysis | | Multivariate analysis | |
|---|---|---|---|---|
| | Odds Ratio (95% CI) | P value | Odds Ratio (95% CI) | P value |
| Age: ≥40 vs <40 years old | 2.521 (1.126-5.647) | 0.0246 | 1.079 (0.408-2.858) | 0.8776 |
| Sex: Woman vs Man | 1.266 (0.638-2.512) | 0.4991 | | |
| Genotype: C vs B | 1.721 (0.911-3.250) | 0.0944 | | |
| HBsAg: ≥3 vs <3 $\log_{10}$ IU/mL | 0.218 (0.096-0.492) | 0.0002 | 0.369 (0.145-0.939) | 0.0364 |
| HBV DNA: ≥6 vs <6 $\log_{10}$ IU/mL | 0.334 (0.174-0.641) | 0.0010 | 0.832 (0.376-1.843) | 0.6511 |

TABLE 10-continued

Factors associated with fibrosis stages 3 and 4 in the patients with CHB

| Variables | Univariate analysis | | Multivariate analysis | |
|---|---|---|---|---|
| | Odds Ratio (95% CI) | P value | Odds Ratio (95% CI) | P value |
| Fatty liver:<br>Yes vs No | 0.653<br>(0.351-1.217) | 0.1799 | | |
| ALT:<br>≥5 × vs <5 × ULN | 0.158<br>(0.068-0.366) | 0.0001 | 0.206<br>(0.080-0.532) | 0.0011 |
| Total bilirubin:<br>≥1.2 vs <1.2 mg/dL | 0.689<br>(0.356-1.333) | 0.2687 | | |
| Platelet:<br>≥150 vs <150 × $10^3$/μL | 0.254<br>(0.132-0.490) | 0.0001 | 0.327<br>(0.156-0.687) | 0.0032 |
| AFP:<br>≥20 vs <20 ng/mL | 1.000<br>(0.997-1.004) | 0.8145 | | |
| FIB-4:<br>≥1.45 vs <1.45 | 2.035<br>(0.945-4.381) | 0.0694 | | |
| APRI:<br>≥1 vs <1 | 0.548<br>(0.295-1.019) | 0.0573 | | |
| CLEC18: pg/mL | 1.000<br>(0.999-1.000) | 0.0883 | | |
| CLEC18:<br>320-2000 vs<br><320 or >2000 pg/mL | 0.629<br>(0.280-1.413) | 0.2611 | | |
| CLEC18: ≥320 vs <320 pg/mL | 0.466<br>(0.217-1.000) | 0.0501 | 0.519<br>(0.210-1.285) | 0.1564 |

In conclusion, the present disclosure provides novel methods for making a diagnosis as to whether a subject has HBV infection, HBeAg loss/seroconversion, and/or fibrosis. Based on the present methods, the clinical practitioner may administer to a subject in need thereof (for example, the subject having HBV infection, chronic hepatitis B and/or liver fibrosis) a suitable treatment in time thereby improving the life quality or the life span thereof.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of diagnosing and treating severe liver fibrosis in a subject having chronic hepatitis B, comprising,
   - (a) isolating a biological sample from the subject;
   - (b) measuring the protein level of CLEC18 in the biological sample;
   - (c) determining the severity of liver fibrosis in the subject based on the measured protein level of CLEC18 in step (b), wherein when the protein level of CLEC18 is lower than 320 pg/mL, then the subject has severe liver fibrosis; and
   - (d) administering to the subject having severe liver fibrosis as determined in the step (c) a treatment selected from the group consisting of, interferon (IFN), lamivudine, adefovir, entecavir, telbivudine, and tenofovir.

2. The method of claim 1, wherein the biological sample is a plasma sample.

3. The method of claim 1, wherein the subject is a human.

* * * * *

```
                    SEQUENCE LISTING

<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: synthesized

<400> SEQUENCE: 1
gatcaagagc cagaaagtgc a                                        21

<210> SEQ ID NO 2
<211> LENGTH: 25
<212> TYPE: DNA
<213> ORGANISM: Artificial Sequence
<220> FEATURE:
<223> OTHER INFORMATION: synthesized

<400> SEQUENCE: 2
gacatcctcg ccttctatct gggcc                                    25

<210> SEQ ID NO 3
<211> LENGTH: 28
<212> TYPE: DNA
<213> ORGANISM: Artificial Sequence
<220> FEATURE:
<223> OTHER INFORMATION: synthesized
```

```
<400> SEQUENCE: 3
gcaaaacccg araaccgtta catctgcc                                      28
```